(12) United States Patent
Seppälä

(10) Patent No.: US 6,886,560 B1
(45) Date of Patent: May 3, 2005

(54) MOISTURE PROTECTED POWDER INHALER

(75) Inventor: Kari Seppälä, Helsinki (FI)

(73) Assignee: Orion Corporation, Espoo (FI)

(*) Notice: Subject to any disclaimer, the term of this patent is extended or adjusted under 35 U.S.C. 154(b) by 0 days.

(21) Appl. No.: 10/070,933

(22) PCT Filed: Sep. 15, 2000

(86) PCT No.: PCT/FI00/00778

§ 371 (c)(1),
(2), (4) Date: Jul. 26, 2002

(87) PCT Pub. No.: WO01/21238

PCT Pub. Date: Mar. 29, 2001

(30) Foreign Application Priority Data

Sep. 17, 1999 (FI) .............................................. 19991981

(51) Int. Cl.[7] ............................................ A61M 15/00
(52) U.S. Cl. ............................ 128/203.15; 128/203.12; 128/203.21; 128/203.23
(58) Field of Search ....................... 128/200.16, 200.14, 128/200.12, 203.23, 203.24, 203.21, 203.15, 203.12; 604/58

(56) References Cited

U.S. PATENT DOCUMENTS 5,201,308 A * 4/1993 Newhouse ............. 128/203.15
5,447,151 A * 9/1995 Bruna et al. ........... 128/203.15

FOREIGN PATENT DOCUMENTS

| EP | 0 166 294 | 1/1986 |
| EP | 0 826 386 | 3/1998 |
| GB | 2 265 552 | 10/1993 |
| WO | WO 90/02576 | * 3/1990 |
| WO | WO 92/18188 | * 10/1992 |
| WO | WO 93/24166 | 12/1993 |
| WO | WO 93/25258 | 12/1993 |

* cited by examiner

Primary Examiner—Henry Bennett
Assistant Examiner—Amanda Wieker
(74) Attorney, Agent, or Firm—Finnegan, Henderson, Farabow, Garrett & Dunner, LLP

(57) ABSTRACT

A powder inhaler comprising a powder container, an air channel, a metering member equipped with a dosing recess, an actuating means for the displacement of the metering member between the filling and the inhalation position, and a closure element for plugging the air channel in a substantially water-proof manner when the metering member is in the filling position and opening the air channel when the metering member is in the inhalation position. When the inhaler is not in use, the closure element prevents moisture and dirt from entering the sensitive parts of the device.

14 Claims, 5 Drawing Sheets

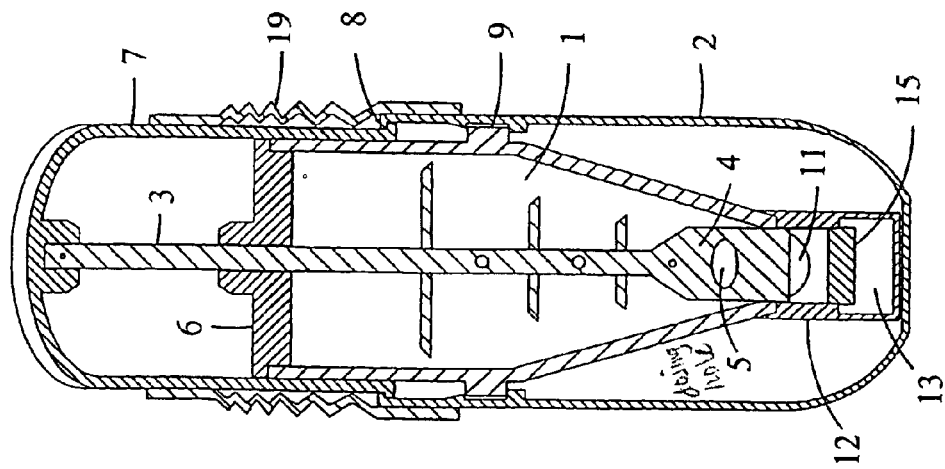
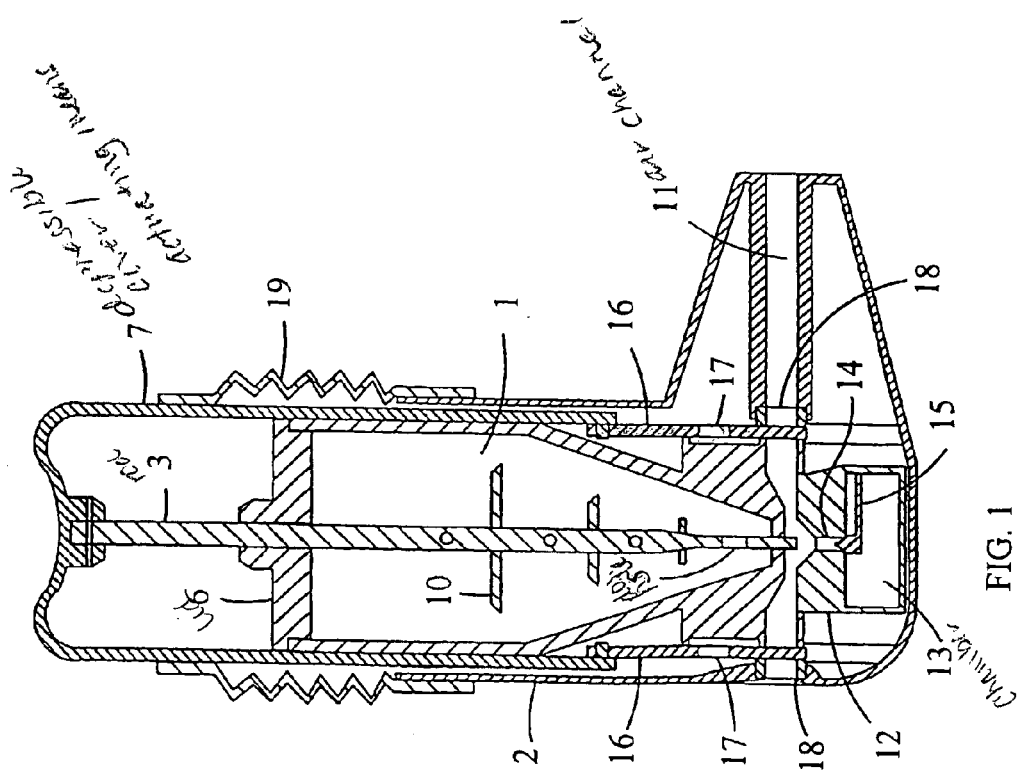
FIG. 1
FIG. 2

MOISTURE PROTECTED POWDER INHALER

This application is a national stage filing of PCT International Application No. PCT/FI00/00778, filed on Sep. 15, 2000. This application also claims the benefit of priority to Finnish patent application no. 19991981, filed on Sep. 17, 1999.

BACKGROUND OF THE INVENTION

The present invention relates to a device for dispensing of a powdered drug preparation by inhalation. The device is in particular a multiple-dose device without propellant gas, equipped with a metering means, which dispenses doses from a powder container. The device of the invention is useful, for example, in the treatment of asthma.

The administering of a powdered drug preparation by inhalation from an inhaler is known. Multidose type powder inhalers comprising a drug container and a metering member for measuring and dispensing a unit dose are also known, for example from patent publications GB 2165159, EP 79478, and EP 166294. In these devices, a series of dosing recesses are notched into the surface of a cylindrical metering member, and the said member is disposed in a chamber of precisely the same shape. When the metering member is rotated, the dosing recesses in turn will move first to a position in alignment with the powder container for being filled and thereafter to a position in alignment with the inhalation channel, whereupon a unit dose will fall by gravity from the dosing recess into the inhalation channel. Thereafter the dose of medicament is inhaled from the inhalation channel. These devices have the drawback that they make overdosing of the medicament possible by allowing the dispensing of a plurality of doses in succession into the inhalation channel, whereby a multiple dose may be drawn by one inhalation.

Attempts have been made to solve the above-mentioned problem by using dispensing systems in which the dosing recess will not be emptied into the inhalation channel by gravity but, instead, the dose of medicament is inhaled directly from the dosing recess, such recesses having been notched into the surface of a metering member having the shape of a cylinder, a cone or a truncated cone, as disclosed in patent publications WO 92/00771 and WO 92/09322. Also in these devices, a metering member having the shape of a cylinder, a cone or a truncated cone is disposed in a chamber having precisely the same shape. When the metering member is rotated, the dosing recesses will move first to a position in alignment with the flow container for filling, and then to the inhalation channel, which is shaped so that the dosing recess will be emptied under the effect of the air flow being inhaled, and thereafter, having rotated through a full 360°, back to a position in alignment with the flow container. Since the metering member is, for purposes of metering precision, disposed within a chamber of the same shape, and since it has to be rotated through 360°, the metering member may be prone to jamming as powder falls onto the surfaces of the device.

The above problem is at least partly avoided in multidose powder inhalers having a metering member in the form of a slide or a rod movable in its longitudinal direction. Such devices have been described e.g. in patent publications EP 758911 B, WO 97/17097, U.S. Pat. No. 5,447,151, U.S. Pat. No. 5,263,475, U.S. Pat. No. 5,765,552 and WO 92/18188. The metering rod or slide equipped with a dosing recess may extend through the interior of the medicament container or it may slide below the orifice of the medicament container.

The above devices have a drawback that they are sensitive to external moisture, which can have a detrimental effect on the measuring accuracy of the device. If a powdered medicament is moistened, e.g. during storage or use of the device, it may form lumps which results in incomplete filling of the dosing recess. Furthermore, if the internal surfaces which are in contact with the discharging medicament powder, e.g. the metering member and the air channel, become moist, the amount of the medicament can be reduced to a fraction of the normal. The moistening may be a result of e.g. an exhalation through an inhaler. For keeping the device free of moisture or dirt, the devices usually have a protective cover, which must be opened before use.

SUMMARY OF THE INVENTION

The object of the present invention is to construct a multidose powder inhaler which avoids the above mentioned disadvantages. The sensitive parts of device of the invention are well protected against moisture and dirt, and, consequently, the device has good metering accuracy and provides complete discharge of the powdered dose into the breathing air. Furthermore, the device of the invention can be stored without protective covers or other elements, which hamper the use of the inhaler.

This is achieved by providing a device for dispensing powdered medicament by inhalation, comprising a powder container;

an air channel through which air is drawn via a mouthpiece;

a metering member equipped with a dosing recess, the metering member being movable between a filling position in which the dosing recess is filled with powder, and an inhalation position, in which the filled dosing recess is brought into the air channel, wherein the stream of inhaled air discharges the dose of powder directly from the dosing recess;

an actuating means for the displacement of the metering member between the filling and the inhalation position; and a closure element for plugging the air channel in a substantially water-proof manner when the metering member is in the filling position and for opening the air channel when the metering member is in the inhalation position.

In the device of the invention the sensitive parts of the device, i.e. the parts that are in contact with the powdered medicament, such as the air channel, the metering member and the medicament container are isolated from the environment by means of the closure element. When the inhaler is not in use, the closure element plugs the air channel in a substantially water-proof manner so as to prevent moisture and dirt entering the sensitive parts of the device. Preferably the closure element comprises a pair of closure elements plugging the air channel firstly at the area of air intake and secondly at the area of air outlet. In this way the metering member with the dosing recess, the orifice of the powder container communicating with the metering member and the air channel, at least in the vicinity of the dosing area, are isolated from the environment.

An actuating means is a means operable by the user for the displacement of the metering member between the filling and the inhalation position. The actuating means may be in the form of e.g. a projection or device cover depressable by the user. It also possible that the metering member is directly operable by the user in which case the metering member is also the actuating means.

The actuating means preferably communicates or is connected with the closure element. The terms "communicate" and "connected" mean herein communicating or being connected either directly or indirectly via another element, e.g. the metering member. The movement of the actuating means by the user results to the movement of the metering member as well as the closure element.

When the actuating means is operated, e.g. depressed by the patient, for measuring a dose of powdered medicament from the container and for transferring it to the air channel for the inhalation, the air channel is opened. This may be carried out by the movement of the closure member to a position in which it no more plugs the air channel. After the inhalation the actuating means is released whereby the air channel is again closed by the closure member which moves back to the plugging position. In this way the sensitive parts of the device are always automatically protected against moisture and dirt as well as against exhalation through the device when the device is not actuated.

The metering of the medicament dose by the metering member can be constructed in number of ways. Also the movement of the metering member by the actuating means between the first and the second positions can be achieved in number of ways.

In one preferred embodiment of the invention the metering member, which is e.g. in the form of a rod equipped with a dosing recess, extends into the interior of the medicament container. In the first position of the rod the dosing recess is inside the medicament container and receives a metered dose of the powdered medicament. In the second position the filled dosing recess is brought from the medicament container to an air channel. The metering rod is engaged with a device cover forming the actuating means that can be depressed by the patient. Alternatively, the metering rod extends through the cover and itself forms a depressable projection acting as an actuating means. Depressing of the actuating means causes metering rod to move from one position, e.g. the filling position, to another position, e.g. the inhalation position.

Alternatively, the metering member, which is e.g. in the form of a longitudinally movable metering strip, is disposed on flat surface below the medicament container as described e.g. in patent publications EP 758911 B and WO 97/17097. The metering strip equipped with a dosing recess slides between the filling and inhalation position below the bottom orifice of the medicament container. In the first position the dosing recess of the metering strip is in alignment with the bottom orifice of the medicament container whereby powder can fall through the orifice to the dosing recess. In the second position the dosing recess is brought to the air channel whereby the metered powder is discharged to the inhaled air from the dosing recess while the metering strip is in the second position. Again, as shown in EP 758911 B, the metering strip may be e.g. engaged with the device cover forming the actuating means or the metering strip extends through the device wall to form itself a depressable projection.

Alternatively, the metering member can be in the form of a rotatable metering drum equipped with one or more peripheral dosing recesses to receive in one position a dose of medicament from the powder container and to bring in another position the medicament to the air channel as described in WO 92/00771 and WO 92/09322.

Also other constructions, suitable for use in the device of the invention, of the metering member or for moving the metering member by the actuating means between the first and the second positions are conceivable to one skilled in the art.

The actuating means preferably communicates or is connected with the closure element so as to transfer the movement of the actuating means by the user to the closure element. Preferably the closure element is able to plug, in one position, the air channel both at the area of air intake and air outlet in a substantially water-proof manner so as to provide moisture protection for the metering member, the powder container as well as the air channel, at least in the vicinity of the dosing area.

The term "plugging the air channel in a substantially water-proof manner" means here that the entry of water via the air channel in an amount that would have a detrimental effect on the measuring and discharging properties of the device is prevented when the air channel is plugged. Preferably the entry of any moisture via the air channel is prevented when the air channel is plugged.

The form of the closure element depends on the dimensions and structure of the air channel. The requisite for the closure element is that it is in a form suitable to plug the air channel in a substantially water-proof manner in one position and is movable between the plugging and non-plugging positions.

In order to secure the substantially water-proof plugging of the air channel by the closure element, the contact area of the closure element and the wall portion of the air channel is preferably equipped with a sealing means. For example, a seal, e.g. an elastic seal ring, can be fitted between the closure element and the wall portion of the air channel. Preferably the sealing means also comprises a means for pressing the closure element tightly against the seal ring as the actuator returns to its rest position.

In one preferred embodiment the closure element consists of a plate equipped with a hole. The plate is connected to the actuating means, which is in the form of a depressable device cover. The plate is slidably mounted across the tubular air channel at the area of air outlet. When the inhaler is not actuated, i.e. the depressable cover is in its rest position, the plate plugs the air channel. When the inhaler is actuated, i.e. the device cover is depressed, the closure plate slides axially downwards until the hole of the plate is in alignment with the cross-section of the tubular air channel. The air channel is open and the dose ready to be inhaled. When the dose has been inhaled and the depressable cover released, the closure plate slides again to the rest position and plugs the air channel. The plugging can be secured with an elastic seal ring and a means for pressing the closure plate tightly against the seal as described above.

Another closure plate is preferably mounted similarly at the area of air inlet, whereby the closure element consists of a pair of parallel plates both connected to the depressable cover.

In order to make the whole device substantially moisture protected when not in use, the device preferably comprises means for providing substantially water-proof sealing also between the actuating means and the inhaler body while allowing the movement of the actuating means in relation to the inhaler body. Such sealing may be e.g. in the form of an elastic tube with a central section comprising a corrugated wall. The elastic sealing tube is attached, at its one end, around the actuating means and, at its other end, around the inhaler body. The corrugated central section of the elastic sealing tube allows the longitudinal dimension of the tube to be reduced to some extent so as not to hamper the movement of the actuating means in relation to the inhaler body.

BRIEF DESCRIPTION OF THE DRAWINGS

FIG. 1 is a cross sectional side view of the device of the invention in the filling position.

FIG. 2 is a cross sectional front view of the device of FIG. 1.

DETAILED DESCRIPTION OF THE INVENTION

Figure 3:
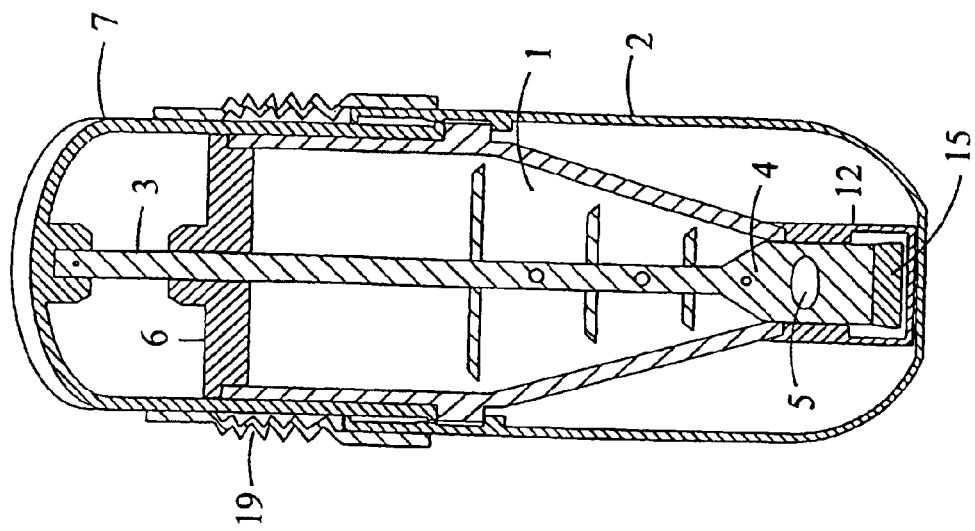
FIG. 3 is a cross sectional side view of the device of the invention in the inhalation position.

The device of the invention is further illustrated below by way of examples, with reference to FIGS. 1 to 9.

FIGS. 1 and 2 show a multidose powder inhaler with a medicament container (1) having a certain supply of powdered medicament. The container has a square cross-section and a conical end portion and is secured to an outer casing (2) by snapfastening means. Normally, the container has a supply of medicament for e.g. 200 doses. A dosing rod (3) having a flattened lower portion (4) with a dosing hole (5) is slidably mounted in the container so that it extends through the lid (6) and through the interior of the container. The bottom wall of the container has a slot adapted to receive the flattened lower portion (4) of the dosing rod (3). The upper end of the rod is fixed to a depressable cover (7) serving as an actuating means. The cover is attached to the outer casing (2) by snapfastening means e.g. such as a peripheral lip (8) which puts an upward limit on the movement of the rod. The rod is urged upwards by a spring (not shown) bearing firstly against the cover (7) and secondly against the lid (6). The downward limit on the movement of the rod is put by the projection (9) of the container.

Figure 6:
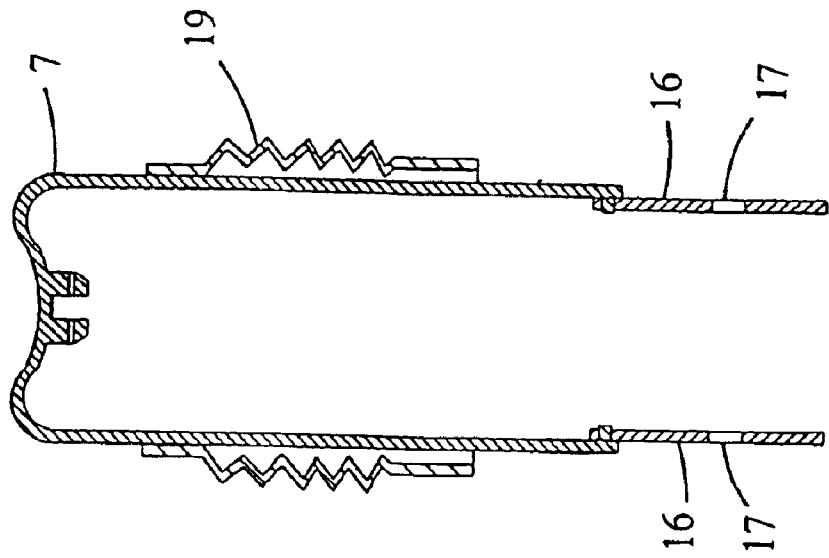
FIG. 6 is a cross sectional side view of the actuating means and the closure element of FIG. 5.
Figure 5:
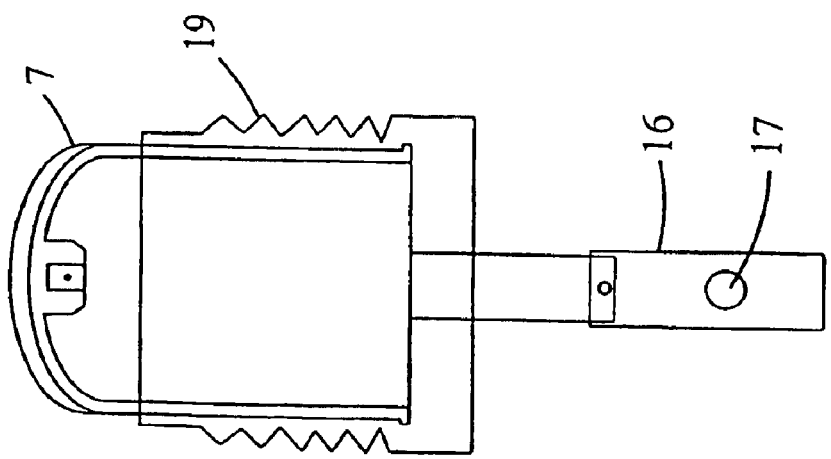
FIG. 5 is a transparent front view of the actuating means and the closure element of the device of the invention.

A pair of closure plates (16) provided with a hole (17) is connected to the cover (7) as more clearly shown in FIGS. 5 and 6. The function of the closure plates is to plug the air channel when the metering member is in the filling position and to open the air channel when the metering member is in the inhalation position, as will be explained later. The closure plates are slidably mounted across the air channel (11) and move in guides that cross the wall of the air channel. Fitted between the wall of the air channel (11) and the closure plate (16) is an elastic seal in the form of a ring (18).

The aperture between the cover (7) and the outer casing (2) is closed with an elastic tube (19) comprising a corrugated wall in the central section and a smooth wall in the end portions. The smooth end portions of the elastic tube attach, at one end, to the surface of the cover (7) and, at another end, to the outer casing (2). This provides a substantially waterproof sealing between the depressable cover (7) and the outer casing while allowing the necessary movement of the depressable cover in relation to the inhaler body.

The dosing rod has projections (10) for agitation of the powder in the container as the rod slides between its first and second position. This agitation effectively prevents the powder arching ("ceiling effect"), which would hinder the flow of the powder towards the dosing hole.

The outer casing (2) defines a mouthpiece through which air is drawn via an air channel (11). Below the medicament container the air channel is defined by an element (12) containing a chamber (13) for the remnants of powder. The element (12) has an aperture (14) corresponding with the slot of the container bottom so that the flattened lower portion (4) of the dosing rod (3) is guided through the slot to the aperture (14). The air channel extends through the element (12) and through the mouthpiece as a tube. The aperture (14) leads to the chamber for remnants (13) into which remnants of powder left in the inhalation channel tends to fall by gravity. The chamber of remnants (13) is closed with a closure member in the form of a strip (15) resiliently mounted on the wall of the chamber (13). The strip (15) is engaged with the tip of the metering rod (3).

FIGS. 1 and 2 show the dosing rod (3) in its upper (filling) position wherein the dosing hole (5) of the dosing rod is in the medicament container for receiving powder. The flattened lower portion (4) of the rod extends slightly through the slot of the container bottom thereby preventing the flow of powder through the slot. The closure plates (16) connected to the depressable cover (7) are in the upper position to plug the air channel. The lower end of the closure plates is suitably formed such that the closure plates are pushed against the sealing ring (18) as they return to the plugging position. This is achieved by gradually increasing the thickness of the plate towards its lower end in the direction opposite to the sealing ring (18) such that the thickened portion forms a wedge-like element that abuts against the pushing surface arranged on the wall of the air channel. Details of the means for pressing the closure plates (16) tightly against the sealing ring (18) are better shown in FIGS. 7–9, which are referred to later.

Figure 4:
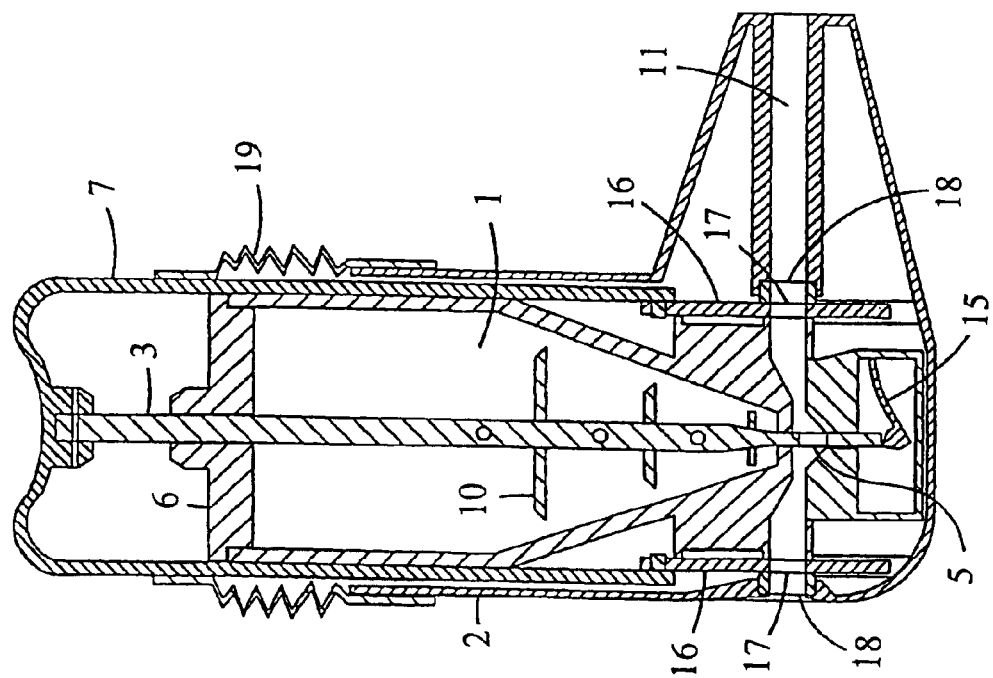
FIG. 4 is a cross sectional front view of the device of FIG. 3.

FIGS. 3 and 4 show the dosing rod in its lower (inhalation) position wherein the cover (7) has been depressed against the spring and the dosing hole (5) has moved to the air channel (11). The tip of the flattened portion (4) of the dosing rod has entered the opening (14) and moved the strip (15) to a position where any powder on the strip (15) tends to fall by gravity to the bottom of the chamber of remnants (13). The dosing hole has stopped at the level of the slanted floor of the air channel and the dose is ready to be inhaled via mouthpiece. At the same time, the closure plates (16) connected to the cover (7) have moved in the guide slot to the position where the holes (17) are lowered to the level of the air channel (11). The diameter of the holes (17) corresponds to the diameter of the air channel (11) such that the air channel is opened for inhalation. The corrugated wall of the elastic tube (19) is in a compressed state so as to follow the movement of the depressed cover (7). The inhalation is effected while the cover is depressed. Substantially all inhaled air streams through the dosing hole and the powder is discharged into the air stream directly from the dosing hole.

After inhalation the cover (7) is released and the metering rod (3) is returned to the filling position by force exerted by the spring. At the same time, the closure plates (16) connected to the cover (7) are drawn upwards in the guide slot to the plugging position. The corrugated wall of the elastic tube (19) is now expanded so as to follow the movement of the depressed cover (7).

As the metering rod returns to the filling position, the strip (15) closes the chamber of remnants. At the same time any remnants of the powder left in the slanted portion of the air channel tend to fall through the aperture (14) to the surface of the strip (15) and upon the next return of the metering rod finally into the chamber of remnants.

Figure 7:
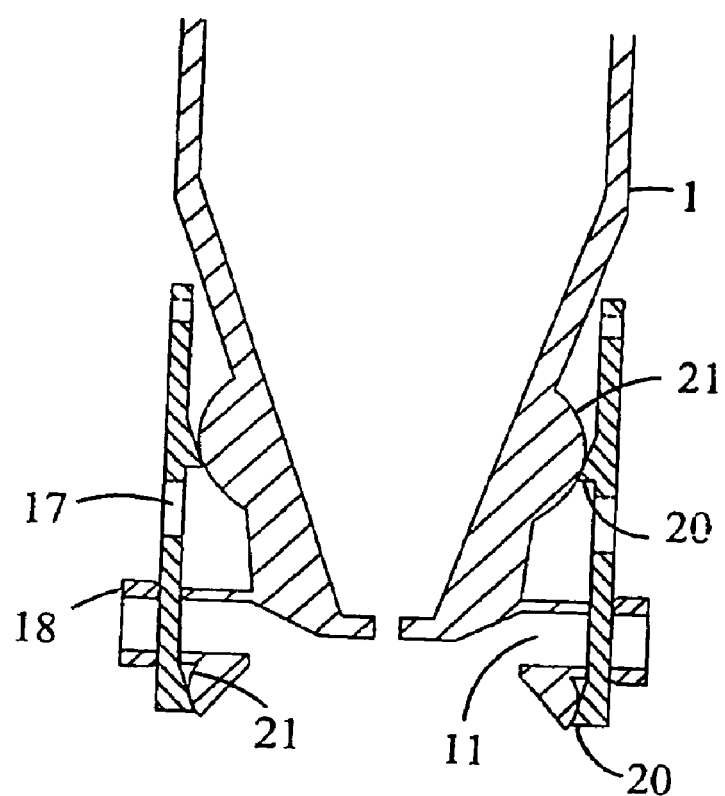
FIG. 7 is a cross sectional side view of one embodiment of the first sealing means.

FIG. 7 shows one embodiment of the means for pressing the closure plates (16) tightly against the seal (18). The closure plates (16) are in their upper position the actuator being released. Each closure plate (16) is equipped with a wedge-like element (20), which is formed by gradually increasing the thickness of the plate towards its lower end in the direction opposite to the sealing ring (18). Another similar wedge-like element (20) is positioned on the closure plate (16) at the area above the hole (17). The wedge-like elements (20) abut against the pushing surfaces (21) arranged on the wall of the air channel (11) and on the wall of the container (1), whereby the closure plates (16) are tightly pushed against the elastic seal ring (18) in a substantially water-proof manner.

Figure 9:
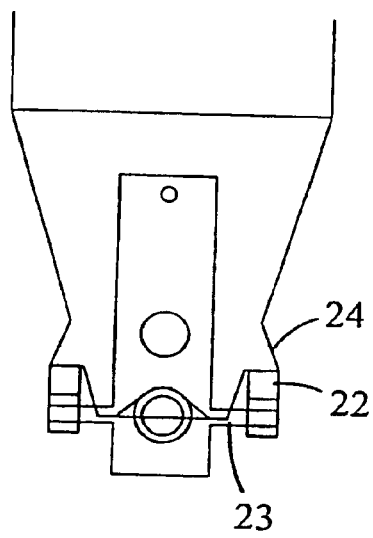
FIG. 9 is a front view of the structure of FIG. 8.
Figure 8:
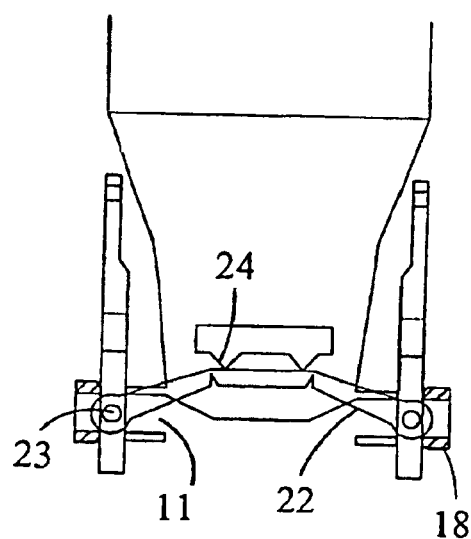
FIG. 8 is a side view of another embodiment of the first sealing means.

FIGS. 8 and 9 show another embodiment of the means for pressing the closure plates (16) tightly against the seal ring (18). In this embodiment the closure plates (16) are connected with two partially flexible bridge elements (22). The bridge elements are mounted on axles (23) extending from the closure plates (16). Pushing surfaces (24) are arranged such that upon the return of the closure plates (16) to their upper position the pushing surfaces (24) cause the bridge element (22) to be straightened slightly. Thereby the closure plates (16) are pushed tightly against the seal ring (18) in a substantially water-proof manner.

Other modifications and variations can be made to the disclosed embodiments without departing from the subject of the invention as defined in the following claims. For example, a counter could be mounted to the inhaler to count the number of pressing of the actuating means. It is considered to be routine for one skilled in the art to make such modifications to the device of the invention.

What is claimed is:

1. A powder inhaler, comprising a powder container;

an air channel through which air can be drawn via a mouthpiece;

a metering member equipped with a dosing recess, the metering member being movable between a filling position in which the dosing recess can be filled with powder, and an inhalation position, in which the dosing recess, when filled, can be brought into the air channel, wherein a stream of inhaled air can discharge a dose of powder directly from the dosing recess;

actuating means for the displacement of the metering member between the filling and the inhalation position; and a closure element adapted to plug the air channel around the metering member in a substantially water-proof manner, so as to protect the air channel around the metering member from moisture, when the metering member is in the filling position, and to open the air channel when the metering member is in the inhalation position, wherein operation of the actuating means results in the movement of the metering member as well as the closure element.

2. A powder inhaler according to claim 1, comprising first sealing means to secure the substantially water-proof plugging of the air channel by the closure element.

3. A powder inhaler according to claim 1, wherein the closure element is in the form of a closure plate connected to the actuating means.

4. A powder inhaler according to claim 1, wherein the closure element is in the form of a pair of closure plates connected to the actuating means.

5. A powder inhaler according to claim 3, wherein the closure plate is equipped with a hole and is slidably mounted across the air channel.

6. A powder inhaler according to claim 2, wherein the first sealing means comprises an elastic seal fitted between the closure element and the wall portion of the air channel and means for pressing the closure element tightly against the seal when the inhaler is not actuated.

7. A powder inhaler according to claim 6, wherein the means for pressing the closure element tightly against the seal comprises a wedge-formed element extending from the closure plate and adapted to contact with a pushing surface as the actuator returns to its rest position.

8. A powder inhaler according to claim 1, wherein the metering member extends into the interior of the powder container.

9. A powder inhaler according to claim 8, wherein the metering member is in the form of an axially movable metering rod equipped with a dosing recess.

10. A powder inhaler according to claim 9, wherein the actuating means is a depressable device cover to which the metering rod is connected.

11. A powder inhaler according to claim 2, further comprising an inhaler body, and further comprising second sealing means for providing substantially water-proof sealing between the actuating means and the inhaler body while allowing the movement of the actuating means in relation to the inhaler body.

12. A powder inhaler of claim 11, wherein the second sealing means is in the form of an elastic tube comprising a corrugated wall.

13. A powder inhaler according to claim 1, comprising first sealing means to secure substantially water-proof plugging of the air channel by the closure element.

14. A powder inhaler according to claim 4, wherein the closure plate is equipped with a hole and is slidably mounted across the air channel.

* * * * *